US005723325A

United States Patent [19]
Murtfeldt et al.

[11] Patent Number: 5,723,325
[45] Date of Patent: Mar. 3, 1998

[54] INDOLYL-3-ALKANE ALPHA-HYDROXYLASE COMPOSITIONS FROM PSEUDOMONAS XA

[75] Inventors: Robert L. Murtfeldt, La Canada; Allan J. Bream; Kathryn K. McCarthy, both of Long Beach, all of Calif.

[73] Assignee: Automedix Sciences, Inc., Irvine, Calif.

[21] Appl. No.: 648,620

[22] Filed: May 16, 1996

Related U.S. Application Data

[60] Continuation of Ser. No. 122,041, Sep. 14, 1993, abandoned, which is a division of Ser. No. 528,681, May 23, 1990, Pat. No. 5,244,807.

[51] Int. Cl.$^6$ .............. C12N 11/14; C12N 9/14; C12N 1/20; C12N 1/06
[52] U.S. Cl. .............. 435/176; 435/177; 435/178; 435/180; 435/195; 435/253.3; 435/259; 435/802; 435/814; 435/818; 435/874
[58] Field of Search .............. 435/174, 178, 435/180, 189, 195, 253.3, 259, 802, 814, 818, 874

[56] References Cited

U.S. PATENT DOCUMENTS

| | | | |
|---|---|---|---|
| 4,431,428 | 2/1984 | Schmer | 424/484 X |
| 4,438,198 | 3/1984 | Schmer | 435/178 |
| 4,955,857 | 9/1990 | Shettigar | 530/412 X |
| 4,956,290 | 9/1990 | Harrison, Jr. et al. | 435/189 |
| 5,244,807 | 9/1993 | Murtfeldt et al. | 435/253.3 |

OTHER PUBLICATIONS

Roberts, et al., The Journal of Biological Chemistry, vol. 252, No. 8, 1977, pp. 2460–2647.
Schmer, et al., Biochimica et Biophysica Acta, vol. 527, 1978, pp. 264–271.
Schmer, et al., Karger, Basel, 1983, pp. 284–297.
Noda, et al., J. Biol. Chem., 252:4413–4415 (1977).
Rosenfeld, et al., J. Biol. Chem., 252:6970–6973 (1977).

*Primary Examiner*—David M. Naff
*Attorney, Agent, or Firm*—Thomas Fitting

[57] ABSTRACT

Compositions containing two species of indolyl-3-alkane alpha-hydroxylase (INDH) are isolated from Pseudomonas XA. An INDH1 composition contains protein subunits having molecular weights of 75,000, 34,500 and 32,500 daltons. An INDH2 composition contains protein subunits having molecular weights of 60,000, 44,000 and 42,000 daltons. Molecular weights are determined by sodium dodecyl sulfate-polyacrylamide gel electrophoresis. The compositions have a Specific INDH Activity of at least 10 international Units of INDH activity per milligram of protein, and contain less than 1 nanogram of endotoxin per International Unit of Specific INDH Activity. The INDH compositions may be immobilized on an insoluble matrix such as silica beads to provide at least 2.5 international Units of INDH activity per gram of Immobilized INDH composition. The INDH compositions are isolated by lysing Pseudomonas XA cells at a temperature of no more than 15° C. to form a solution containing INDH, separating INDH from the solution at a temperature of no more than 15° C. to form an isolated solution of INDH, determining protein concentration of the isolated solution, and if the protein concentration is less than 1 mg/ml, concentrating the solution such as by ultrafiltration to increase the protein concentration to within the range of 1 to 10 mg/ml.

8 Claims, 3 Drawing Sheets

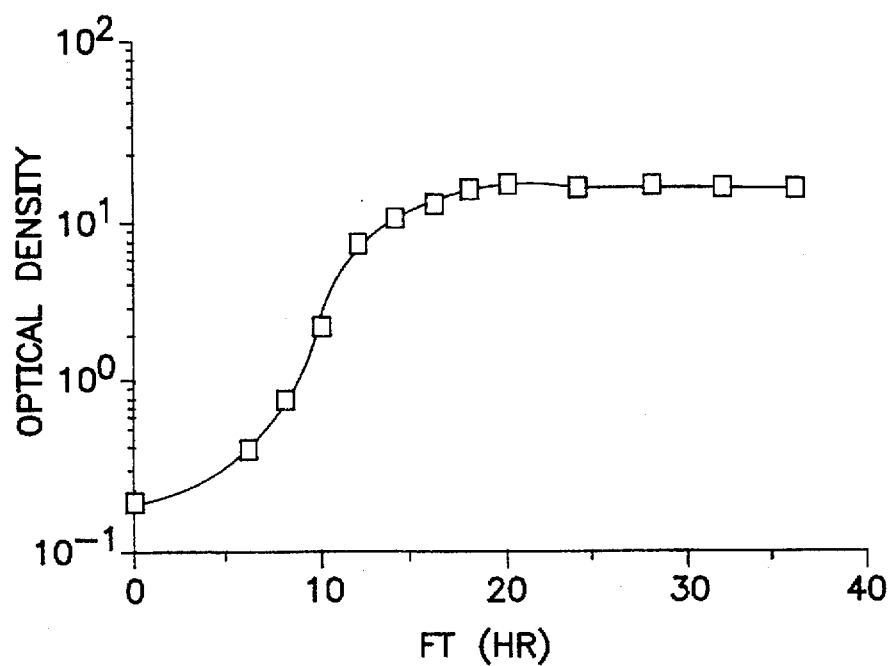
FIG. IA
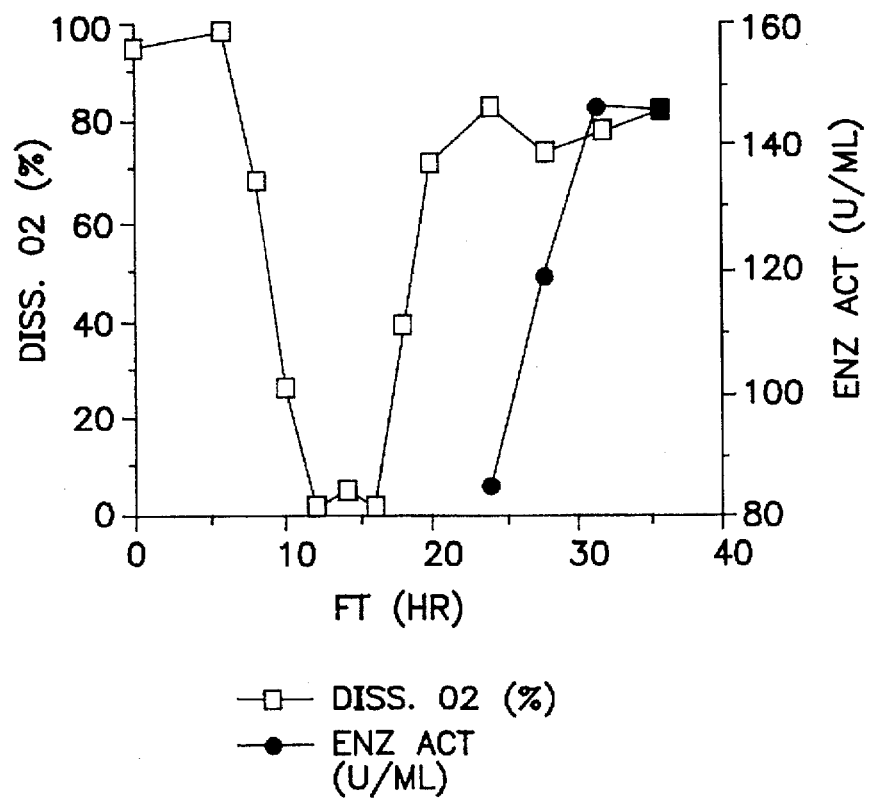
FIG. IB

INDOLYL-3-ALKANE ALPHA-HYDROXYLASE COMPOSITIONS FROM PSEUDOMONAS XA

This is a continuation of application Ser. No. 08/122,041, filed Sep. 14, 1993, now abandoned, which is a division of application Ser. No. 07/528,681, filed May 23, 1990, now issued U.S. Pat. No. 5,244,807.

TECHNICAL FIELD

The present invention relates to compositions containing substantially isolated indolyl-3-alkane alpha-hydroxylase (INDH) enzyme and methods of preparing INDH enzyme. More particularly, the present invention contemplates substantially isolated INDH1, substantially isolated INDH2, compositions comprising the combination of INDH1 and INDH2, particularly endotoxin-free compositions, and methods of using the compositions.

BACKGROUND

L-tryptophan (tryptophan), or alpha-amino-beta-3-indolylproprionic acid, is an essential amino acid in mammals, is present in most proteins, and is found in various mammalian tissues, including the blood and the brain.

Enzymatic removal of tryptophan from solutions, such as blood, as by plasmapheresis and extracorporeal treatment by enzymatic degradation of the tryptophan in the pheresed blood, has long been perceived to have therapeutic benefits. For example, blood levels of tryptophan modulate synthesis and synaptic release of the neurotransmitter serotonin. Varying tryptophan blood levels provides a means to affect brain serotonin levels. Wurtman et al., U.S. Pat. No. 4,435,425; and Gessa et al., Acta. Vitamin Enzymol., 29:72–78 (1975). In addition, a body of research suggests that reduced dietary or blood levels of tryptophan will inhibit growth of malignant neoplasms. Wooley et al., Cancer Res., 34:1010–1014 (1974); and Schmer et al., in "Plasma Separation and Plasma Fractionation", pp 284–297, Karger, Basel (1983).

Various enzymes are known that enzymatically degrade tryptophan, including indolyl-3-alkane-alpha-hydroxylase (INDH) and tryptophan side chain oxidase (TSO).

Both TSO and INDH enzymes have been isolated from the Pseudomonas species known as Pseudomonas XA. The isolated enzymes have been characterized to varying degrees by different groups. See, for example, Takai et al., Meth. in Enzymol., 142:195–217 (1987); and Roberts et al., J. Biol. Chem., 252:2640–47 (1977).

TSO has been characterized as being comprised of two species, referred to as TSO I and TSO II, each being prepared from Pseudomonas XA, and each being characterized as multienzyme complexes containing heme that catalyze essentially similar reactions involving tryptophan as a substrate. However, TSO I and TSO II are distinguishable by their subunit structure and antigenicity, and by their reactivity with and specificity for various substrates, indicating that TSO I and TSO II are distinct enzymes. Takai et al., Meth. in Enzymol, 142:195–217 (1987).

INDH has been characterized as comprising a tryptophan-metabolizing enzyme of about 250,000 daltons in molecular weight. No protein subunit data is available for INDH. Roberts et al., J. Biol. Chem., 252:2640–47 (1977).

Methods and systems for treating blood to deplete tryptophan that utilize immobilized enzyme in an extracorporeal device (artificial bioreactors) have been described. See, for example, U.S. Pat. No. 4,438,198; and Schmer et al., in "Plasma Separation and Plasma Fractionation", pp 284–297, Karger, Basel (1983). However, stability of INDH enzyme activity was not achieved when the enzyme was immobilized by chemical crosslinking means to a matrix suitable for use in an extracorporeal device. In addition, endotoxin contamination was reported in an INDH-containing bioreactor that produced a histamine-like syndrome usually found when blood contacts with endotoxin. Schmer et al., in "Plasma Separation and Plasma Fractionation", pp 284–297, Karger, Basel (1983). Because of the complications associated with biological responses to endotoxin, it is desirable that INDH enzyme be free of endotoxin-mediated side effects.

BRIEF SUMMARY OF THE INVENTION

An INDH enzyme has now been prepared in a composition that is stable, free from endotoxin-mediated side effects and has sufficient specific activity to be useful for the depletion of tryptophan from aqueous solutions, preferably blood or plasma.

Thus, the present invention contemplates an INDH enzyme composition obtainable from Pseudomonas XA that comprises a substantially isolated INDH enzyme, has a Specific INDH Activity of at least 10 International Units (IU) of INDH enzyme activity per milligram (mg) of enzyme in the composition, and contains less than 1 nanogram (ng) of endotoxin per IU of Specific INDH Activity.

The substantially isolated INDH enzyme is selected from the group of INDH enzymes consisting of:

(a) an INDH1 enzyme having a first, second and third protein subunits, the first protein subunit having a molecular weight of about 75,000 daltons, the second protein subunit having a molecular weight of about 34,500 daltons, and the third protein subunit having a molecular weight of about 32,500 daltons, all as determined by sodium dodecyl sulfate-polyacrylamide gel electrophoresis; and (b) an INDH2 enzyme having a first, second and third protein subunits, the first protein subunit having a molecular weight of about 60,000 daltons, the second protein subunit having a molecular weight of about 44,000 daltons, and the third protein subunit having a molecular weight of about 42,000 daltons as determined by sodium dodecyl sulfate-polyacrylamide gel electrophoresis. In preferred embodiments, an INDH enzyme composition comprises a combination of INDH1 and INDH2 enzymes.

In another embodiment, the invention contemplates an immobilized INDH composition comprising an insoluble matrix, and an INDH enzyme composition as described above that is affixed to the insoluble matrix, said immobilized INDH composition having at least 2.5 IU, and preferably at least 15 IU, of INDH enzyme activity per gram of immobilized INDH composition, and having less than 10 ng, preferably less than 0.1 ng, of endotoxin per IU of INDH enzyme activity present in the immobilized INDH composition.

The invention also contemplates a method of reducing the concentration of tryptophan in an aqueous solution, preferably human plasma, comprising the steps of contacting the aqueous solution with an immobilized INDH composition of this invention to form a liquid-solid phase reaction admixture, maintaining the reaction admixture for a predetermined time period and under reaction conditions sufficient for any tryptophan present in the liquid phase to be degraded by the action of the INDH enzyme present in the immobilized INDH composition, and then recovering the liquid phase free of said immobilized INDH composition. In preferred embodiments of the tryptophan depleting method the contacting, maintaining and recovering steps are conducted by the continuous flow of the aqueous solution over a predetermined amount of said immobilized INDH composition present in an extracorporeal device adapted to contain the composition and to allow extracorporeal plasma to flow into, through and out of said device.

The present invention provides several benefits and advantages. An INDH enzyme having the disclosed minimum specific activity provides more efficient tryptophan depletion when used in an extracorporeal device or when used in vivo, as compared to enzyme preparations having lower activity.

The claimed INDH enzyme has demonstrated stability when exposed to body fluids such as blood, providing the advantage that less enzyme is required in methods requiring prolonged fluid contact.

An important benefit of INDH enzyme having the indicated minimum specific activity is that the patient is exposed to less enzyme mass per unit of INDH enzyme activity and thereby is exposed to less endotoxin in a given treatment. Reduced exposure to endotoxin results because the disclosed INDH enzyme composition has low endotoxin per unit of INDH enzyme activity. Thus the patient can be exposed to greater amounts of INDH enzyme activity without risking endotoxin-induced histamine-response type side effects.

BRIEF DESCRIPTION OF THE DRAWINGS

FIGS. 1a and 2a are semi-logarithmic plots of Pseudomonas XA growth over 36 hours in culture as described in Example 1a. The fermentation time (FT) in hours (HR) is on the X axis and the logarithmic optical density scale at 550 nm is on the Y axis. FIGS. 1b and 2b are graphs in which the percentage of dissolved oxygen (DISS. 02 (%)) (open squares) measured as described in Example 1a are plotted on the left Y axis over fermentation time (FT) in hours (HR) plotted on the X axis. Assayed INDH enzyme activity as described in Example 1c(2) is plotted on the right Y axis against FT. Enzyme activity is measured in units/ml (U/ml) (closed triangles).

Figure 2A:
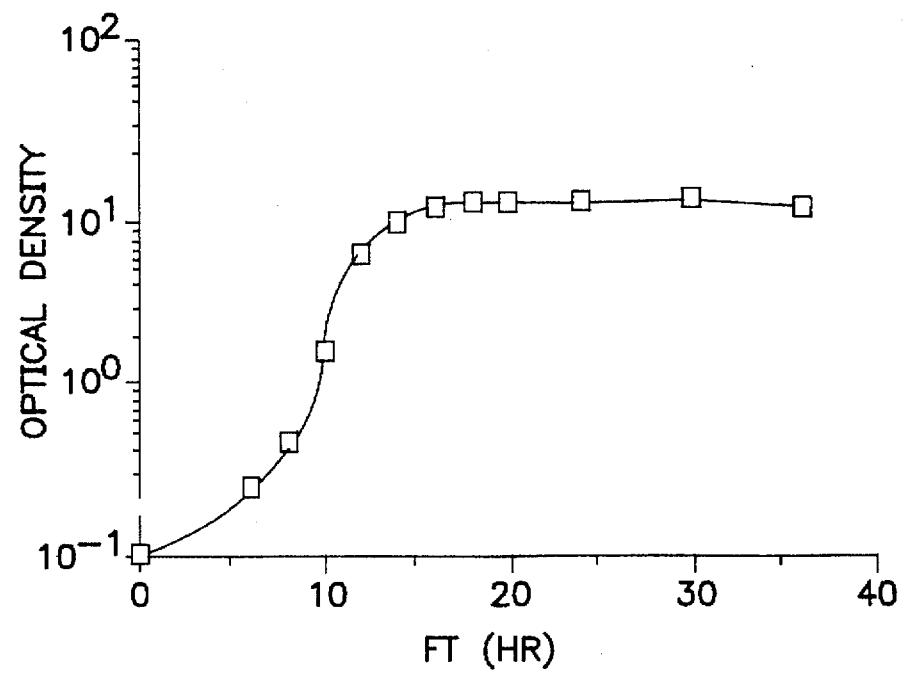

Lanes 1 and 10 contain the following MW marker proteins: rabbit muscle phosphorylase B, 97.4; bovine serum albumin, 66.2; hen egg white ovalbumin, 42.699; bovine carbonic anhydrase, 31.0; soybean trypsin inhibitor, 21.5; and hen egg white lysozyme, 14.4, all in units of one thousand daltons.

Lanes 2–5 contain increasing amounts of purified INDH2 enzyme from about 1.3 ug to about 13 ug. Lanes 6–9 contain decreasing amounts of purified INDH1 enzyme from about 16.7 ug to about 1.7 ug.

DETAILED DESCRIPTION OF THE INVENTION

A. INDH Enzyme Compositions

In one embodiment, the invention contemplates an INDH enzyme composition comprising substantially isolated INDH enzyme.

INDH refers to an enzyme which hydroxylates substrate at the side chain carbon adjacent to the indole ring on a variety of 3-substituted indole compounds in a stepwise fashion. Rosenfeld et al., *J. Biol. Chem.*, 252:6970–73 (1977); and Nada et al., *J. Biol. Chem.*, 252:4413–15 (1977). Stepwise, INDH first acts like an oxidase and produces an olefinic intermediate having a double bond between the indole 3 position and the adjacent side chain carbon to form a 3-alkylidene indoline. Thereafter, a 1,4-addition of water to the indoline results in the hydroxylation of the substrate.

Substrates that are hydroxylated by INDH include tryptophan, N-acetyltryptophanamide (NATA), tryptophan methyester, tryptophol, indole-3-propionate, indole-3-butyrate, and tryptophan-containing di- and oligopeptides. Roberts et al., *J. Biol. Chem.*, 252:2640–47 (1977). The enzymatic reaction typically conducted by methods of the present invention is the hydroxylation of tryptophan substrate to form a degradation product.

The substantially isolated INDH enzyme present in an INDH enzyme composition of the present invention can refer to two distinguishable and separable INDH enzymes designated herein as INDH1 and INDH2. Therefore, a composition comprising an INDH enzyme, as defined herein, can contain an INDH1 enzyme, an INDH2 enzyme, or both. Unless the specific INDH enzyme (i.e., INDH1 or INDH2) is identified, the use of the phrase "INDH enzyme" is therefore intended to refer interchangeably to INDH1 enzyme and INDH2 enzyme, or combinations of INDH1 and INDH2 enzymes.

The INDH1 and INDH2 enzyme compositions described herein each exhibit the enzymatic activity described above, as does a composition containing the combination of INDH1 and INDH2 enzymes described herein.

The INDH1 enzyme contains three protein subunits, having relative molecular weights of about 75,000 daltons, about 34,500 daltons and about 32,500 daltons, respectively, as determined by sodium dodecyl sulfate-polyacrylamide gel electrophoresis (SDS-PAGE) using rabbit muscle phosphorylase B, bovine serum albumin, hen egg white ovalbumin, bovine carbonic anhydrase, soybean trypsin inhibitor, and hen egg white lysozyme as comparative molecular weight standards. That is, the electrophoretic mobility of the protein subunit components present in an INDH1 enzyme of the present invention exhibits the identified relative molecular weights when compared to the co-electrophoresed molecular weight standards. The technique and reliability of molecular weight determination by SDS-PAGE are well known in the art. Laemmli, (*Nature*, 227:680, 1971); Weber et al., *J. Biol. Chem.*, 244:4406 (1969); and Zwaan, *Anal. Biochem.*, 21:155 (1967)).

The INDH2 enzyme contains three protein subunits, having relative molecular weights of about 60,000 daltons, about 44,000 daltons and about 42,000 daltons, respectively, as determined by SDS-PAGE using as comparative molecular weight standards those named above for INDH1.

An INDH enzyme present in a composition of this invention is further characterized as being substantially isolated. A composition comprising a substantially isolated INDH enzyme has a minimum specific activity attributable to an INDH enzyme, i.e. a Specific INDH Activity. Therefore, a composition having substantially isolated INDH enzyme is characterized as having a Specific INDH Activity of at least 10 international units (IU), and preferably at least 25 IU, of INDH enzyme activity per milligram (mg) of enzyme in the composition.

Methods for determining Specific INDH Activity of an INDH enzyme are well known in the art but may vary depending on the enzyme assay reaction conditions, particularly the reaction temperature and substrate used to detect INDH enzyme activity. Specific INDH Activity is expressed herein as IU when measured using the substrate NATA according to the methods described in Example 1c.

A composition comprising a substantially isolated INDH enzyme is further characterized as having no more than a maximum amount of endotoxin per IU of Specific INDH Activity in order that the INDH enzyme can be useful without adverse side effects. Endotoxins are also referred to as lipopolysaccharides (LPS). Endotoxins have a broad spectrum of biological activity. In particular, endotoxins are toxic in humans and other animals and can induce fever (i.e., they are pyrogenic), allergy and sweating when present in trace amounts, and can cause hypotensive shock, disseminated intravascular coagulation, and, in some cases, death. Because of their biological activity and the fact that they are derived from gram negative bacteria, endotoxins are a potential contaminant of any aqueous solution.

The presence of endotoxins in compositions containing INDH enzyme, therefore, are undesirable. A composition having substantially isolated INDH enzyme is characterized herein as containing less than 1 nanogram (ng) per IU of Specific INDH Activity, preferably less than 0.04 ng per IU, and more preferably less than 0.01 ng per IU.

Assay of endotoxin activity can be accomplished by a variety of means well known in the art, such as the Limulus amoebocyte lysate (LAL) assay and the United States Pharmacopeia rabbit pyrogen test (The Pharmacopeia of the United States of America, 17th Revision, 863, 1965), U.S. Pat. No. 4,276,050 to Firca et al. A preferred LAL assay is the PYROTEL gel clot assay used herein and available from Associates of Cape Cod (Woods Hole, Mass.).

B. Preparation of Substantially Isolated INDH Enzyme

One aspect of the present invention pertains to a process for preparing substantially isolated INDH enzyme. The process entails first preparing a crude mixture containing INDH enzyme, then fractionating the mixture containing the enzyme, and monitoring the resulting solution so fractionated for the presence of Specific INDH Activity as described herein.

1. Culturing Pseudomonas XA

Solutions containing INDH enzyme are first obtained by culturing a bacterial source followed by extraction of the INDH enzyme from the bacterial culture. Species of Pseudomonas are known to produce INDH enzyme activity. A preferred source of INDH is Pseudomonas XA, preferably the strain available from the American Type Culture Collection (Rockville, Md.), having an accession number 29574. Cultures of Pseudomonas XA can be prepared as described by the ATCC, or according to the teachings of Schmer et al., *Biochem. Biophys. Acta*, 527:264–271 (1978), or as described herein below in Example 1a.

In one embodiment the invention contemplates a method for producing a culture of Pseudomonas XA bacterial cells containing INDH enzyme for use in preparing an INDH enzyme composition. To practice the method, the Pseudomonas XA cells are cultured in an aerobic batch fermentation process as disclosed herein. The aeration rate is adjusted during the fermentation process such that the combination of oxygen consumption and aeration occurring in the culture produces an oxygen starvation condition in the culture for a time period of about two to seven hours during the logarithmic phase of the culture. Preferably, the oxygen starvation condition (time period) ends at the beginning of the saturation phase of the culture.

In preferred embodiments, the oxygen starvation condition is produced for about five hours beginning from about 11 hours after the inoculation in a culture that would normally progress from inoculation to saturation in about 16 hours, and preferably in a 36 hour fermentation process such as is disclosed herein. Exemplary are the growth conditions and growth curves described in Example 1 and shown in FIG. 1.

An oxygen starvation condition, as used herein, is a culture condition where the dissolved oxygen is maintained at a level of less than 10 percent, and preferably at about 2 to 7 percent, of the dissolved oxygen present in the culture prior to inoculation with Pseudomonas XA innoculum. An oxygen starvation condition can be produced by a variety of means, but is conveniently produced by adjusting the aeration rate of the culture during the fermentation process at the same time as the dissolved oxygen is being measured as to regulate the dissolved oxygen levels in the culture. In preferred embodiments, a single aeration rate is predetermined and is maintained throughout the fermentation process, such as for both the 5700 liter and the 1600 liter processes described in Example 1a.

Dissolved oxygen is measured by conventional oxygen sensors adapted for measurement in liquid cultures. Ten percent dissolved oxygen is defined as an amount of oxygen detectable in a fermentation culture solution (i.e., dissolved oxygen) that is one tenth the amount of dissolved oxygen detectable in similar solution having 100 percent dissolved oxygen. One hundred percent dissolved oxygen is an amount of dissolved oxygen detectable in a fermentation culture solution when measured in the culture before it has been inoculated with bacteria and after that culture has been equilibrated to the proper fermentation process conditions of temperature, aeration, pH and back pressure as disclosed herein. A dissolved oxygen level of 100 percent is also referred to as a saturated level of dissolved oxygen.

Thus, in a method for producing a culture of Pseudomonas XA bacterial cells containing INDH enzyme, the present invention contemplates subjecting the culture to an oxygen starvation condition during the fermentation process to boost enzyme levels in the cells prior to harvest. The method comprises: (1) culturing the cells in an aerobic batch fermentation process, said cells having a logarithmic phase and a stationary phase in the process; (2) measuring the dissolved oxygen concentration of the culture at the beginning of the fermentation process, when said culture has a saturated level of oxygen, to determine a first oxygen concentration; and (3) adjusting the degree the aeration in the culture to produce a second oxygen concentration (i.e., an oxygen starvation condition) in the culture of about two to seven percent of said first oxygen concentration for a time period of about two to about seven hours, said time period ending at the beginning of the stationary phase. In preferred embodiments, the time period for an oxygen starvation condition is about five hours in duration. Logarithmic phase, when used to describe a bacterial cell fermentation process, refers to a time period in the fermentation process where the cell density increases approximately logarithmically over a linear period of time.

Stationary phase, when used to describe a bacterial cell fermentation process, refers to a time period in the fermentation process where the cell density remains substantially constant in the culture. Stationary phase begins when the cell density in the culture reaches about 95 to 100 percent of the maximum possible cell density in the culture.

2. Isolation of INDH Enzymes from Pseudomonas XA

A solution containing INDH enzyme is typically prepared by extraction of the INDH enzyme from Pseudomonas XA cells in a bacterial culture. To that end, Pseudomonas XA cells treated with a bacterial cell lysing means under bacterial cell lysing conditions are first homogenized in isotonic nondenaturing buffers so as to release the INDH enzyme from within the bacterial cell to form a solution containing INDH enzyme and contaminants. Typical bacterial cell lysing means include the use of mechanical disruption, as by sonication or homogenization using a high pressure homogenizer, or by the use of denaturing solvents such as detergent-containing solutions. Preferred are the lysing means described in Example 1b that involve both homogenization and proteolytic digestion with typsin that were conducted under the disclosed conditions that are suitable for lysing bacterial cells.

Residual cells and debris are separated from the obtained solution containing INDH enzyme by means of a variety of biochemical and physical chemical separation techniques well known in the art which rely upon the above-described characteristics for the INDH enzyme. A preferred method of isolating the INDH enzyme is described in Example 1b, although similar biochemical fractionation methods, such as gel filtration, gel chromatography, ultrafiltration, ion exchange chromatography, and the like, such as are known for protein fractionation can be used as manipulative steps to separate the INDH enzyme from other proteins (contaminants) present in the solution containing INDH enzyme.

Of particular importance throughout the purification procedure for INDH enzyme are considerations that preserve maximum Specific INDH Activity in the INDH enzyme. Throughout the course of purification, it was determined that isolation of an INDH enzyme for use in the present invention having the required Specific INDH Activity involved constantly maintaining the INDH enzyme-containing solutions at cold temperatures, preferably below 15 degrees Centigrade (15 C.), and more preferably at about 4 C., and maintaining the INDH enzyme protein concentrations in the INDH enzyme-containing solutions at greater than 1 mg/ml of solution, and preferably greater than 3 mg/ml. During those fractionation steps in which the INDH enzyme was diluted to less than 1 mg/ml, the manipulations were carried out expeditiously to minimize the time in which the INDH enzyme was exposed to dilute solution and thereafter was concentrated by ultrafiltration so as to restore protein concentrations at least above 1 mg/ml.

Thus, in one embodiment the present invention contemplates a method for isolating an INDH enzyme from a Pseudomonas XA bacterial cell culture that results in producing an INDH enzyme composition comprising substantially isolated INDH enzyme having the Specific INDH Activity disclosed herein. The isolation method comprises (1) treating a Pseudomonas XA bacterial cells with a lysing means under bacterial cell lysing conditions at a temperature of no more than 15 C. to form a solution containing INDH enzyme and contaminants; (2) separating and recovering at a temperature of no more than 15 C. the INDH enzyme from said solution formed in step (1) to form an isolated solution of INDH, wherein said separating and recovering comprises a series of manipulative steps that each form an isolated solution of INDH (i.e., an INDH enzyme-containing solution); (3) determining the concentration of protein present in the INDH enzyme-containing solution formed in step (2); and (4) subjecting the isolated solution of INDH enzyme to a predetermined amount of protein concentration increasing means if said determined protein concentration is less than 1 mg/ml, said predetermined amount being an amount sufficient to raise the protein concentration of the solution to within the range of 1 mg/ml to 10 mg/ml.

Protein concentrations can be determined by methods well known, and are determined after a manipulative step in the isolation procedure, and preferably after any step that results in a dilution of total protein concentration.

Of particular importance to the present embodiment is determining the protein concentrations after a chromatographic manipulative step because of the extent of dilution accompanying that procedure. Representative are the hydrophobicity chromatography or S-Sepharose chromatography steps described in Example 1b. These chromatographic steps are important to monitor for protein concentration and to make the indicated adjustments because the INDH enzyme is no longer in the presence of high protein concentrations, and most particularly after the S-Sepharose chromatography because ammonium sulfate is no longer present, which is also known to stabilize proteins.

Protein concentration increasing means are those manipulations whereby the concentration of protein in a solution is changed or adjusted to a predetermined level. A protein concentration can be adjusted by a variety of means including methods for reducing fluid volumes such as by ultrafiltration using an ultrafiltration means, evaporation, and the like volume reducing means, and alternatively by increasing total protein concentrations by the addition of carrier proteins, such as serum albumins and the like methods for adjusting protein concentrations. Exemplary of a protein concentration increasing means is the ultrafiltration carried out as described in Example 1b. In ultrafiltration, liquid is removed from an isolated solution of INDH enzyme and the INDH enzyme is retained in the solution by an ultrafiltration membrane A variety of INDH enzyme purification protocols have been described in the published literature, although none have produced an INDH enzyme-containing composition having the characteristics described herein. See, for example, Schmer et al., *Biochem. Biophys. Acta*, 527:264–271 (1978); and Roberts et al., *J. Biol. Chem.*, 252:2640–47 (1977).

In preferred embodiments, INDH enzyme are isolated according to the procedures described in Example 1, incorporating the above considerations regarding culture conditions, temperature and protein concentration throughout the enzyme preparation and purification procedure.

The isolation of the two species of INDH, namely INDH1 and INDH2, can be accomplished by a column chromatography fractionation step in which a solution containing both species of INDH enzyme is resolved over an ion-exchange resin having a strong cation exchanger, and having a capacity to resolve high molecular weight proteins in the molecular weight range of at least 20,000 to 75,000 daltons. A preferred resin, as described in Example 1, is one similar to the S-Sepharose Fast-Flo ion exchange resin (Pharmacia LKB, Piscataway, N.J.). By fractionation of a solution containing both INDH1 and INDH2 on such an ion exchange resin, the isolated INDH enzyme-containing solutions are eluted from the column, presenting an elution profile showing two major peaks; one having a pH of 4.2 and containing INDH2 enzyme, and the other having a pH of 5.2 and containing INDH1 enzyme.

At the stage where INDH1 and INDH2 enzymes are isolated away from each other, such as after the above ion exchange chromatography separation step, the enzymes can each be separately purified further to remove contaminants as disclosed herein. Alternatively, the separate INDH1 and INDH2 enzyme preparations can be combined to form an INDH enzyme having both INDH1 and INDH2 enzymes, and that combined enzyme can be subjected to further purification. It is preferred that INDH1 and INDH2 enzyme-containing solutions be combined after ion exchange chromatography and prior to further purification manipulations.

The preparation of an INDH enzyme having reduced amounts of contaminating endotoxin is necessary for an INDH enzyme composition of this invention. Various well known methods for removing endotoxins from biological molecules present in aqueous solution are suitable for use in the preparation of a subject INDH enzyme composition, so long as the method does not substantially reduce the specific activity of the enzyme. Methods using affinity chromatography with polymyxin B linked to insoluble carriers, such as agarose, are preferred and are well known. See for example, Niwa et al., *Japan J. Med. Sci. Biol.*, 35:114–116 (1982); Issekutz et al., *J. Immunol. Methods*, 61:275–281 (1983). Particularly preferred are methods that utilize polymyxin B-based affinity chromatography in combination with a dialyzable surfactant as to desorb any endotoxin away from the biological molecule of interest. See Karplus et al., U.S. Pat. No. 4,808,314, and the method described herein at Example 1b.

Throughout the endotoxin removal step and thereafter, it is required that all buffers, glassware and other materials that come into contact with a purified INDH enzyme composition be endotoxin-free. By endotoxin-free is meant that the buffers, glassware or other material tested are negative for endotoxin using the L.A.L. assay as described herein. Methods for removing endotoxins from buffers, glassware and other materials are generally well known and are suitable in the present methods.

C. Immobilized INDH Compositions

The present invention also contemplates an immobilized INDH composition for use in depleting tryptophan from aqueous solutions having tryptophan contained therein.

An immobilized INDH composition comprises an insoluble matrix and an INDH enzyme composition of the present invention affixed to the insoluble matrix.

An immobilized INDH composition is further characterized as having at least 2.5 international Units of INDH enzyme activity per gram (gm) of immobilized INDH composition, preferably at least about 15 International Units per gm.

In addition, an immobilized INDH composition, as disclosed herein, has less than 10 nanograms (ng) of endotoxin per International Unit of INDH enzyme activity present in the immobilized INDH composition, preferably less than 1 ng per IU, more preferably less than 0.25 ng per IU, and still more preferably less than 0.1 ng endotoxin per IU.

An insoluble matrix suitable for use in an immobilized INDH composition can be any of a variety of water-insoluble solid phase matrices. Silica is used herein as an exemplary insoluble matrix, as described in Example 2. However, other particulate and monolithic solid phase matrices are suitable, such as cross-linked agarose, polystyrene or glass beads, cross-linked polyacrylamide, the surfaces of hollow fibers useful in dialysis or ultrafiltration, the matrices disclosed in U.S. Pat. Nos. 4,491,660, 4,381,239 and 3,897, 309, and the amine-reactive polymers described in U.S. Pat. Nos. 3,597,220, 3,597,221, 3,597,351, 3,650,900 and 3,650, 901, and the organic or inorganic matrices disclosed in *Handbook of Enzyme Biochemistry*, Second Edition, A. Weisman, ed., (1985), all of whose disclosures are incorporated by reference.

Although materials vary in the degree of water-solubility, the term "water-insoluble" as used herein connotes in its usual sense that the matrix, and the immobilized INDH composition made therefrom, are able to be recovered substantially intact and in substantially the same amount as that admixed with the aqueous medium when the first solid-liquid admixture is prepared. The matrix can be swellable in water, and can form a gel-like solid phase and still be within the purview of a water-insoluble material as contemplated herein.

In embodiments where the immobilized INDH composition is used by passing tryptophan-containing solutions through volumes of the composition in a column format, it is preferred that the insoluble matrix exhibit the capacity to accommodate the flow of liquids through a volume of an immobilized INDH composition. Thus the insoluble matrix is selected such that the flow rate of a liquid through a device containing about 60 mls of an immobilized INDH composition in a column format is 10 to 300 ml/min with a pressure drop of less than 300 millimeters (mm) of mercury (Hg), and preferably is at least 100 ml/min with a pressure drop of less than 100 mm/Hg.

The manner by which the INDH enzyme complex is affixed to the insoluble matrix can be by a variety of physical or chemical means, so long as an amount of the INDH enzyme composition remains operatively attached to the insoluble matrix throughout manipulations of the immobilized INDH composition in aqueous mediums as to provide the required amounts of Specific INDH Activity and endotoxin content. Preferred attachment means for affixation of the INDH enzyme complex to the insoluble matrix are disclosed in Example 2, and involve covalent chemical bonds. Other suitable covalent attachments include any linkage between a chemical group on the matrix and, for example, an amino group or a carboxyl group present on a protein subunit of an INDH enzyme.

Methods for affixing proteins to an insoluble matrix are well known by skilled artisans and need not be dealt with in detail herein and are suitable for preparing an immobilized INDH composition. illustrative of a preferred affixation method is the procedure described in Example 2. Alternatively, affixation may be accomplished by the use of activated carboxyl groups as are provided by cyanogen bromide treatment of glucose-containing solids and chemical reactions using water-soluble carbodimide technology, glutaraldehyde linking and the like. Additional representative affixation methods and means are described in *Handbook of Enzyme Biotechnology*, Second Edition, A. Weisman, ed. (1985).

An immobilized INDH composition so prepared is useful, inter alia, in the methods disclosed herein for reducing tryptophan in aqueous solutions, such as body fluids.

D. Methods for Reducing Trytophan in Aqueous Solutions

The present invention contemplates a method for reducing the amount of tryptophan in an aqueous solution by the use of the INDH enzyme containing compositions of the present invention.

In one embodiment, the method comprises contacting an aqueous solution, believed to contain tryptophan, with an immobilized INDH composition of the present invention to form a solid-liquid phase admixture where the solid component comprises the immobilized INDH composition by virtue of its water-insolubility. The admixture is then maintained for a predetermined time period under conditions compatible with INDH enzyme reaction sufficient for any tryptophan present in the admixture to be degraded by the enzymatic action of the INDH enzyme present in the immobilized INDH composition. Thereafter, the solid and liquid phases of the maintained admixture are separated, and the liquid phase is retained (recovered), being substantially free of the immobilized INDH composition and having a reduced tryptophan content relative to the aqueous solution.

The contacting can be carried out either by admixture of a preselected volume of aqueous solution with the immobilized INDH composition (i.e., batch mode), or in a continuous flow modality wherein the solution is passed over or across a preselected amount of the immobilized INDH composition (i.e., column mode). In the column mode, the immobilized INDH composition is contained within a column or other reservoir adapted to accommodate an insoluble material that allows a liquid phase to be passed over the insoluble material, and the aqueous solution is loaded onto and continuously eluted from the column to comprise the contacting, maintaining and separating steps in a continuous process. Although a batch mode is suitable for practicing the present method, the column mode is preferred, as it is particularly suited for tryptophan depletion of a liquid phase such as blood or plasma. A more detailed description that is exemplary of the preferred column mode is presented in Example 3.

Maintenance conditions suitable for an enzyme reaction are well known for INDH enzyme, and are enzyme concentration, time, temperature, buffer and pH parameters preselected as to allow an INDH enzyme reaction to proceed. Methods for optimizing such conditions are also well known and can be applied as needed to control the particular rate of enzyme reaction desired. For example, in the embodiment adapted to deplete tryptophan from blood, as described in Example 3, a maximum enzyme reaction rate is desired to minimize endotoxin contact. In that embodiment, a maximum INDH enzyme reaction rate is accomplished by contacting the plasma with immobilized INDH compositions having the maximum possible Specific INDH Activity under conditions optimized for maximum reaction rates.

In a related embodiment, a method for tryptophan in an aqueous solution comprises contacting the aqueous solution with an INDH enzyme composition of the present invention to form a tryptophan reduction admixture. Thereafter the admixture is maintained under enzyme reaction conditions for a predetermined time period sufficient for any tryptophan present in the admixture to be degraded. Although the aqueous solution to be treated can be any solution containing tryptophan, a preferred solution is blood. A preferred means for admixture is to administer, as by injection, an effective amount of an INDH enzyme composition directly into the bloodstream of a mammal in whose blood a reduction of tryptophan is desired.

Therefore, in one version of this embodiment, a therapeutically effective amount, ie., a tryptophan-reducing amount, of an INDH enzyme composition is administered directly (in vivo) to the blood of a mammal in a predetermined amount calculated to achieve the desired effect, i.e., to reduce the blood concentration of tryptophan.

For instance, when used as an agent for reducing blood tryptophan levels, such as in a human patient displaying the symptoms of a malignancy, an INDH enzyme composition is administered in an amount sufficient to achieve a dosage of 0.1 to 200 IU/kg body weight/day, and preferably 70 to 120 IU/kg body weight/day, and more preferably 75 to 95 IU/kg body weight/day when given either as a single dose per course or in incremental doses.

The therapeutic compositions containing an INDH enzyme are conventionally administered intravenously by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject to tolerate and to utilize the active ingredient, and degree of reduction of blood tryptophan levels desired. Precise amounts of active ingredient required to be administered depend on the judgment of the practitioner and are peculiar to each individual. However, suitable dosage ranges for systemic application are of the order of 0.1 to 200, preferably 70 to 120, and more preferably 75 to 95 IU per kilogram bodyweight of individual per day and depend on the route of administration. Suitable regimes for initial administration and booster shots are also variable, but are typified by an initial administration followed by repeated doses at one or more hour intervals by a subsequent injection or other administration such as continuous intravenous infusion.

E. Therapeutic Compositions

The present invention also contemplates therapeutic compositions containing an INDH enzyme as described herein, that is formulated for use in the in vivo injection therapeutic methods described herein above.

The composition, when formulated for in vivo administration, contains a physiologically tolerable carrier together with the substantially isolated INDH enzyme dissolved or dispersed therein as an active ingredient. In a preferred embodiment, the therapeutic composition is not immunogenic when administered to a mammal or human patient.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically, such compositions are prepared as injectables either as liquid solutions or suspensions; however, solid forms suitable for solution, or suspensions, in liquid prior to use can also be prepared. The preparation can also be emulsified.

The active ingredient can be mixed with excipients which are pharmaceutically acceptable and compatible with the active ingredient. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such a sodium phosphate at physiological pH value, physiological saline or both, such as phosphate-buffered saline. Still further, aqueous carriers can contain more than one buffer salt, as well as salts such as sodium and potassium chlorides, dextrose and other solutes.

Liquid compositions can also contain liquid phases in addition to and to the exclusion of water. Exemplary of such additional liquid phases are glycerin, vegetable oils such as cottonseed oil, and water-oil emulsions.

EXAMPLES

The following examples are intended to illustrate, but not limit, the present invention.

1. Preparation of INDH1 and INDH2 Enzyme Composition
a. Aerobic Fermentation of Pseudomonas XA A lyophilized culture of Pseudomonas XA (ATCC #29574; American Type Culture Collection, Rockville, Md.) was reconstituted in 0.5 milliliters (ml) of 0.85% sterile saline to produce a bacterial suspension. The suspension was inoculated onto Nutrient Agar (Difco Laboratories, Detroit Mich.), prepared at 23 grams per liter (gm/l), and maintained at 26 C. for 48 hours. A loop full of cells grown on the Nutrient Agar was collected, admixed with 80 ml of Nutrient Broth (Difco), prepared at 8 gm/l, in a 250 ml flask and the admixture maintained on a gyrorotary shaker at an agitation rate of 200 rotations per minute (rpm) for 16 hours at 26 C. Eighty mls of the admixture was then aseptically transferred into a 12 liter fermenter containing 8 liters of sterilized Nutrient Broth and 0.4 gm of 10% antifoam SAG471 (Union Carbide, South Charleston, W. Va.), and maintained for 16 hours at 26 C. at an agitation rate of 250 rpm and an aeration rate of 1.0 VVM (volume of air per fluid volume per minute) to form a Pseudomonas XA inoculum. Eight liters of the inoculum was then aseptically transferred to (inoculated into) a fermenter containing 5700 liters of a sterile nutrient solution [15 kilograms (kg) glucose; 102 kg pancreatic digest of casein (NZ Case Plus; Sheffield Products, Norwich, N.Y.); 18 kg papaic digest of soybean meal (High Soy; Sheffield Products); 30 kg sodium chloride; 15 kg dipotassium phosphate and 600 g antifoam SAG471] to initiate an aerobic batch fermentation process. The inoculated fermenter was then maintained for 36 hours at 26 C. at an agitation rate of 70–75 rpm, an aeration rate of 0.5 VVM and a back pressure of 5 pounds per square inch (psi). The fermenter was equipped with a pH controller set to maintain the pH at 7.0 to 7.5 throughout the 36 hour culturing (maintenance) step.

The fermenter was also equipped with an oxygen (O2) probe to measure the percentage of dissolved oxygen throughout the 36 hour fermentation process. The oxygen probe was calibrated to one hundred percent oxygen (100% O2) to represent the amount of dissolved oxygen present in the starting culture when measured prior to inoculating the 5700 liter culture indicating a culture saturated with dissolved oxygen. A percentage decrease in the dissolved oxygen during the fermentation represents a linear decrease in the dissolved oxygen relative to the amount dissolved at saturation. Decreases or increases in the percentage of dissolved oxygen were due to the rate consumption of oxygen by Pseudomonas XA and not due to a change in the aeration rate of the 5700 liter culture. In the 5700 liter culture, the dissolved oxygen dropped steeply to about 2 to 7 percent oxygen about 11 hours after inoculation, and then increased steeply to above 70 percent oxygen about 16 hours after inoculation, and remained above 70 percent thereafter until fermentation was stopped. After the 36 hour maintenance step, the admixture was cooled to 8–12 C., the cooled admixture was centrifuged at 12,000×g for 1–3 minutes to form a pellet and the pellet was collected to form pseudomonas cell paste.

Experiments in a 1600 liter Pseudomonas XA culture were performed to determine the effect of fluctuating dissolved oxygen on cell growth and on production of INDH enzyme activity. Two identical 1600 liter cultures (1 and 2) were established as in Example 1a. in both cultures, the aeration rate was held constant at 0.5 VVM. In culture 1, the agitation rate was held constant at 150 rpm for the 36 hour fermentation process. In culture 2, the agitation rate was varied from 150 rpm for the first 11 hours, to 200 rpm for the next five hours, and back to 150 rpm for the last 20 hours. The percentage of dissolved oxygen in both cultures was measured at various time points throughout the 36 hour period. The optical density of the cultures was measured using a spectrophotometer with a 550 nm filter at these same time points as a measurement of changes in cell number. Culture broth samples were collected at four hour intervals beginning at 24 hours after inoculation of the culture to measure INDH enzyme activity. The samples were centrifuged in a clinical centrifuge at 500 rpm for five minutes. The supernatants were discarded and the pellets were resuspended in 50 mM sodium phosphate, pH 7.0 to a concentration of 1 gm/10 ml. The suspensions were sonicated on ice on a high setting three times for 30 seconds each time. The sonicated suspensions were centrifuged in a microfuge of 12,000×g for three minutes. The resulting supernatants were retained as crude lysates and assayed according to the NATA assay described in Example 1c(2).

Figure 2B:
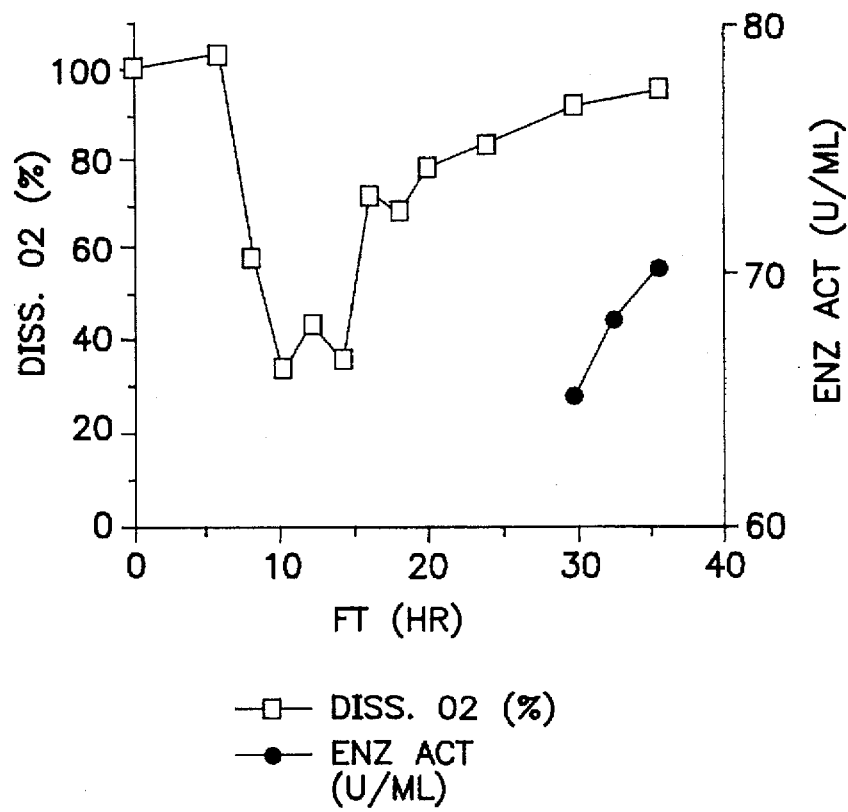

The results of the above fluctuating dissolved oxygen experiments are shown in FIGS. 1 and 2. During the initial growth phase of both of the cultures between 0 and 16 hours of the 36 hour maintenance period (FIGS. 1*a* and 2*a*), the oxygen consumption by Pseudomonas XA increased thereby resulting in a decrease of the percentage of dissolved oxygen (FIGS. 1*b* and 2*b*). A minimum level in dissolved oxygen was observed in both cultures between about 11 and 16 hours of the maintenance period. After about 16 hours, the density of both cell cultures began to increase (FIGS. 1*a* and 1*b*) and then the cells entered into the stationary growth phase which correlated with a decrease in oxygen consumption and an increase in the percentage of dissolved oxygen (FIGS. 1*b* and 2*b*). In culture 1 where the agitation rate was held constant, the dissolved oxygen decreased from greater than 90% to less than 10% between 11 and 16 hours (FIG. 1*b*). During this same time period in culture 2, the increase in the agitation rate from 150 rpm to 200 rpm resulted in an increase in the percentage of dissolved oxygen (FIG. 2*b*). The minimum amount of dissolved oxygen during this low oxygen period at about hours 11–16 was greater than 30% for culture 2 as compared to an oxygen starvation condition of less than 10% for culture 1.

In both cultures after about 20 hours where the agitation rate was 150 rpm, the cells had entered stationary growth phase (FIGS. 1*a* and 1*b*) and the dissolved oxygen stabilized between 70 and 90%. During this stationary phase, samples of the admixture were analyzed for INDH enzyme activity (closed triangles, FIGS. 1*b* and 2*b*). In crude lysates from culture 1, the resultant maximum INDH enzyme activity present in the cells at 36 hours was 140 U/ml (FIG. 1*b*). In crude lysates from culture 2, the enzyme activity at 36 hours reached a maximum of 70 U/ml (FIG. 2*b*).

The two fold increase of enzyme activity in lysates from culture 1 compared to culture 2 was the result of an oxygen starvation condition imposed onto the cells in the initial growth phase that included the logarithmic phase and was not due to an increase in total cell number at the end of the maintenance period. Both cultures had similar densities and growth rates based on measurements of samples taken throughout the 36 hour maintenance period (FIGS. 1a and 2a).

The improved production of INDH enzyme activity resulted from a low dissolved oxygen treatment of the culture prior to the culture entering stationary phase, at about hours 11–16 of the maintenance period. In addition, prolonged saturation for over 16 hours was found to be useful for production of the enzyme.

b. Purification of INDH Enzyme from Pseudomonas Cell Paste

Six kg of pseudomonas cell paste, prepared in Example 1a, was admixed with 30 liters of suspension buffer (0.05M sodium acetate, 0.01M EDTA, 0.2M sodium chloride, pH 6.5) and agitated for at least two hours until a homogeneous cell suspension was formed. The homogeneous cell suspension was adjusted to a volume of about 45 liters with suspension buffer, passed through a high pressure (5,000–6,000 psi) homogenizer, collected and cooled to 10–12 C. using an isopropanol ice bath. The ice bath was occasionally agitated to avoid ice formation. The cooled suspension was again passed through the high pressure homogenizer, collected and adjusted to a volume of 60 liters with suspension buffer precooled to about 12 C. The temperature of the homogeneous cell suspension was then adjusted to 12 C., and the pH adjusted to 6.8–7.2 with 1N sodium hydroxide. The homogeneous cell suspension was then admixed with 18 gm of trypsin powder (bovine trypsin; Waitaki International Biosciences, Toronto, Canada) to form a crude enzyme solution containing INDH enzyme and contaminants. The crude enzyme solution was stirred constantly and 1.0N sodium hydroxide added, as necessary, to maintain pH at 6.8–7.2. Aliquots of the crude enzyme solution were tested every half hour for INDH activity, using N-acetyl tryptophanamide (NATA) as the substrate according to the NATA assay described in Example 1c. Stirring continued until increases in the INDH enzyme activity detectable in solution stabilized, typically after about 2 hours. The crude enzyme solution was then cooled to 4 C. and admixed, with constant stirring, with a composition of Biocryl BPA 1000 (TosoHass, Philadelphia, Penn.) to achieve a BPA level of 7,000–8,000 ppm and to form a BPA-enzyme admixture. Biocryl BPA 1000 is a strongly cationic quaternary amine cross-linked polymeric particle (0.1 micron diameter) composition that absorbs charged species in aqueous solutions. The BPA-enzyme admixture was stirred for five minutes and then centrifuged at 9000 rpm for 20 minutes in a Sorvall RC5, rotor (DuPont, Wilmington, Del.) to form a pellet and supernatant. The resulting supernatant was passed through a high porosity filter to remove cell debris, collected, titrated with ammonium sulfate to a final ammonium sulfate concentration of 1.2M, and agitated at 700–800 rpm for five minutes to form an ammonium sulfate suspension.

A hydrophobicity chromatography column containing 10 liters of Butyl 650-M (TosoHaas, Philadelphia, Penn.) resin was equilibrated with 1.2M ammonium sulfate in 0.05M sodium acetate, pH 6.5 until the conductivity of the eluant measured 86±2 mmho/cm. The above-prepared ammonium sulfate suspension, having a conductivity of at least 88 mmho/cm at 4 C., was added to the column at a rate of 400–500 ml/min. The column was washed with wash buffer (1.2M ammonium sulfate in 0.05M sodium acetate, pH 6.5) at a flow rate of 400–500 ml/min, until the eluant produced an optical density (O.D.) reading at 280 nanometers (nm) of less than 0.2. O.D. units above the baseline of the wash buffer. Eluant buffer (0.6M ammonium sulfate in 0.05M sodium acetate, pH 6.5) was then added to the column at a flow rate of 100–200 ml/min, and the resulting eluant collected in approximately 1,000 ml fractions. Each eluant fraction was analyzed for INDH activity using NATA as the substrate according to the NATA assay in Example 1c, and the eluant fractions containing significant INDH activity were pooled and designated an INDH suspension.

A volume (25 liters) of the INDH suspension was reduced to about 0.5 liter in a 30,000 molecular weight (mw) cut off ultrafilter device (Pellicon; Millipore Corp., Bedford, Mass.) to form a concentrated INDH suspension. The concentrated INDH suspension was then cooled to 4 C. and diafiltered in the same 30,000 mw ultrafilter device with about 5 liters of 0.05M sodium acetate buffer, pH 3.0, precooled to 4 C., to form a diafiltered solution. During diafiltration, temperature, pH and conductivity were measured every 10 minutes. Diafiltration continued until the conductivity of the diafiltered solution was less than 3 mmhos/cm and the pH was 3.2±0.1. The diafiltered solution was then centrifuged at 350×g for 10 minutes to form a diafiltration supernatant.

A chromatography column containing 700 ml of S-Sepharose Fast-Flo resin was prepared and maintained at about 4 C., and was equilibrated with 10–20 column volumes of 0.05M sodium acetate buffer, pH 3.0, precooled to 4 C., until the conductivity of the column eluant was equal to the conductivity of the sodium acetate buffer. The diafiltration supernatant of about 1500 mls was then applied to the S-Sepharose column at a rate of 100–150 ml/min. During the application, and throughout chromatography, the column and column buffers were maintained at 4 C. After application of the supernatant, the column was washed with the sodium acetate buffer at a rate of 100–150 ml/min until the eluant had an O.D. at 280 nm of less than 0.2. O.D. units above the baseline for the sodium acetate buffer. The column was then washed with an additional 10–20 liters of sodium acetate buffer at the same flow rate. The column was then eluted, at a flow rate of 100–150 ml/min, with 16–20 column volumes of a linear pH gradient, from 0.05M sodium acetate, pH 3.0, to 0.5M sodium phosphate, pH 7.0. The eluant was collected in 100–250 ml fractions using pyrogen-free glass bottles. Each fraction was tested for pH and for INDH activity using the NATA assay described in Example 1c. Major peaks of enzyme activity were identified in the fractions having a pH of about 4.2 and at about 5.2. Fractions of pH 4.2 were pooled and designated as pooled INDH2 fractions. Fractions of pH 5.2 were pooled and designated as pooled INDH1 fractions. The concentration of protein was measured in both the pooled INDH1 and pooled INDH2 fractions and determined to be about 0.3 to 0.5 mg/ml. The INDH enzyme activity present in selected fractions is shown in Table 1.

TABLE 1

NATA Enzyme Activity in S-Sepharose Eluant Fractions

| Fraction Number | NATA Enzyme Activity (IU/ml) |
| --- | --- |
| 4 | 1.7 |
| 6 | 7.6 |
| 7 | 8.2 |
| 8 | 6.0 |
| 10 | 1.9 |
| 12 | 2.4 |
| 14 | 10.4 |
| 16 | 25.5 |

TABLE 1-continued

NATA Enzyme Activity in S-Sepharose Eluant Fractions

| Fraction Number | NATA Enzyme Activity (IU/ml) |
|---|---|
| 18 | 20.7 |
| 20 | 5.9 |

A 30,000 MW cutoff ultrafiltration membrane (Millipore) of 10 ft$^2$ was cleaned, depyrogenated and equilibrated with 0.05M sodium phosphate buffer, pH 7.0., at 4 C. Pooled INDH1 fractions were cooled in an ice bath and concentrated on the 30,000 mw cutoff ultrafiltration membrane at a flow rate of 100 ml/min to reduce the volume of the pooled fractions to approximately 300 ml. During the concentration process, the temperature was maintained below 10 C. The resulting concentrated pooled fractions (retentate) were collected. The ultrafiltration membrane was then rinsed with 300 ml of 0.05M sodium phosphate buffer (4C), pH 7.0, and the resulting rinse was collected and combined with the retentate to form a composition of substantially isolated INDH1 enzyme.

The pooled INDH2 fractions were concentrated in a manner identical to the above ultrafiltration of pooled INDH1 to form a composition of substantially isolated INDH2 enzyme.

The protein concentration of the substantially isolated INDH1 or INDH2 enzyme compositions was determined to be about 3 to 5 mg/ml after concentrating by ultrafiltration.

The substantially isolated INDH enzyme (either INDH1 or INDH2) was titrated with sodium deoxycholate (DOC) to a final DOC concentration of 0.1% (w/v) to form a detergent solution. The detergent solution was simultaneously pumped, in parallel, through both a polymyxin B-polymeric matrix (Affiprep; BioRad, Richmond, Calif.) chromatography column (1 volume enzyme per 2 volumes of matrix) and a 30,000 mw cutoff polysulfone ultrafiltration membrane (Millipore), both of which had been equilibrated with 0.1% (w/v) DOC in 0.05M sodium phosphate buffer (4 C) at pH 7.0. The column flow-through and the ultrafilter retentate were continuously recirculated through a reservoir containing the enzyme. The ultrafilter permeate (filtrate) was discarded. The volume of enzyme solution in the reservoir was kept constant by the continuous addition to the reservoir of DOC-free 50 mM sodium phosphate buffer, pH 7.0. This process was continued until 10 volumes of the solution was collected as the ultrafilter permeate. The retentate was collected, designated as purified INDH1 or purified INDH2 enzymes, sterile filtered through a 0.22 micron filter and stored at −80 C. in pyrogen-free glass containers.

An additional INDH enzyme composition was prepared that contained both purified INDH1 enzyme and purified INDH2 enzyme. To that end, INDH enzyme was prepared as in Example 1b, except that the entire range of fractions between and including pH 4.2 and pH 5.2 were pooled to form combined INDH1 and INDH2 pooled fraction. Thereafter, the combined fractions were processed as before for the individual INDH enzyme pooled fractions to form the corresponding purified INDH enzyme, containing INDH1 and INDH2 enzyme. This combined INDH1 and INDH2 enzyme composition is referred to herein as combined INDH1 and INDH2 enzyme.

Three different preparations were separately produced as described above having combined INDH1 and INDH2 enzyme. Each preparation was characterized as described in Example 1c and the relative protein mass of the INDH1 and INDH2 components were estimated based on the relative amounts of those components present on SDS-PAGE gels. The mass ratio, expressed as percent INDH1:percent INDH2, for each of the three preparations was 65:35, 51:49 and 32:68.

Protein concentrations of the variously prepared INDH enzymes containing solutions, whether INDH1, INDH2 or combined, were determined using bicinchoninic acid in a modified Lowry assay as an alternative to the Folin-Ciocalteu reagent as described by Smith et al., *Anal. Biochem.*, 150:76 (1985), and according to the BCA-1 Protein Kit (Sigma Chemical, Co., St. Louis, Mo.) following the manufacturer's instructions.

c. Characterization of Purified INDH Enzyme Compositions
(1) Molecular Weight

The purified INDH1 or INDH2 enzyme prepared in Example 1b were each subjected to SDS-PAGE to determine composition and purity. Samples of purified INDH1 or INDH2 enzyme were diluted at least five fold with SDS gel sample buffer (0.0625M Tris-HCL, pH 6.8, 10% glycerol, 2% SDS, 5% 2-mercaptoethanol, 0.00125% bromophenol blue) such that the diluted protein concentration ranged from about 10 µg per 40 µl down to about 0.1 ug per 40 ul. The diluted sample was then heated at 90–100 C. for two to five minutes. Ten µg of sample protein were loaded onto precast 4–20 percent acrylamide gels (EC1025 from Novex Precast Gel Systems, Encinitas, Calif.). Electrophoresis was performed at a voltage of 200 volts and an amperage of 30 mA until the dye migrated about 6.5 cm to the bottom of the gels. The gels were then stained using coomassie blue and photographed to identify individual bands. The molecular weight of individual enzyme bands was determined by comparison with simultaneously run protein standards (Low Range SDS-PAGE Standards, #161-0304; BioRad). A sample gel is shown in FIG. 3.

Figure 3:
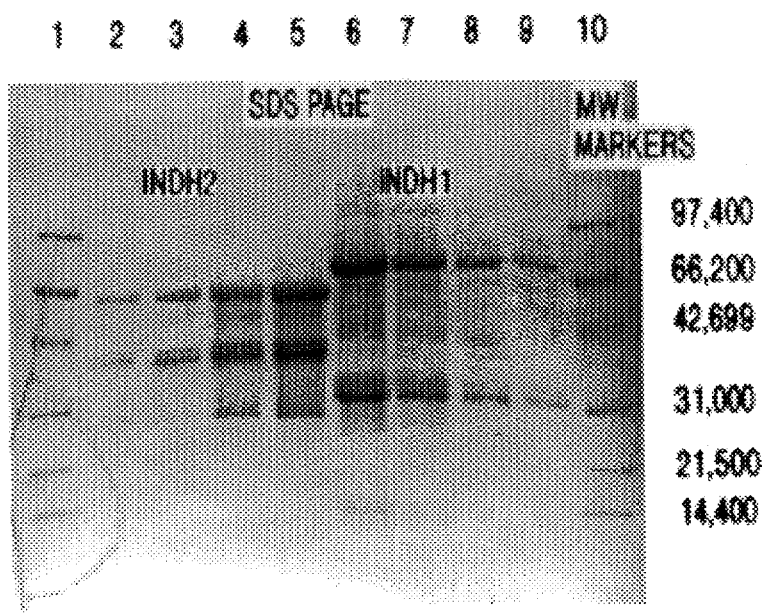
FIG. 3 is a photograph of a 40 to 20 percent SDS-PAGE gel showing the analysis of INDH1 and purified INDH2 enzymes, prepared in Example 1b and characterized as described in Example 1c. The position of molecular weight (MW) marker protein, and their respective relative molecular weights, is shown to the right of lane 10 in units of daltons.

The purified INDH1 enzyme is shown in lanes 6–9 of FIG. 3. All dilutions of INDH1 enzyme were observed to comprise at least three protein subunits, the first having a relative molecular weight of about 75,000 daltons, the second having a relative molecular weight of about 34,500 daltons, and the third having a relative molecular weight of about 32,500 daltons. The purified INDH2 enzyme is shown in lanes 2–5 of FIG. 3. All dilutions of INDH2 enzyme were found to comprise at least three protein subunits. The molecular weights of these INDH2 subunits were observed to be about 60,000, 44,000, and 42,000 daltons, respectively.

(2) INDH Enzyme Activity Assay Using NATA as Substrate

The combined INDH1 and INDH2 enzyme, prepared as described in Example 1b and containing purified INDH1 and purified INDH2 enzyme in a ratio of about 1:1, was analyzed for INDH enzyme activity using N-acetyl-L-tryptophanamide (NATA) as the substrate. Three ml of 1 mM NATA in assay buffer (0.1M sodium phosphate buffer, pH 7.0) were placed in a spectrophotometric cuvette cell having a 1 cm cell path length. Purified INDH enzyme-containing solutions were diluted in assay buffer. One hundred and fifty µl of assay buffer containing various dilutions of the combined INDH1 and INDH2 enzyme were added to the cuvette and mixed by inversion. The absorbance was measured continuously at 333 nm over a period of six minutes. INDH enzyme activity (Specific INDH Activity) is expressed in international Units (IU/mg) and was calculated from the measured change in absorbance using an absorption coefficient for NATA of 19.8 ml/micromole.cm using the following formula:

$$c = A \times V_s \times V \text{ ab } V_r W$$

where:
    c=enzyme activity in IU/mg,
    A=measured change in absorbance per minute,
    a=micromolar absorption coefficient,
    b=cell path length in cm,
    Vs=solute volume in ul, total reaction volume,
    Vr=reactant volume in ul, enzyme sample volume,
    W=weight of enzyme sample in mg in the Vs, and
    V=volume of solute before Vs is added.

Measured in this manner, the Specific INDH Activity of combined INDH1 and INDH2 enzyme was found to be about 25.6 IU/mg. Two other independent preparations of combined INDH1 and INDH2 enzyme were found to have Specific INDH Activities of 26.5 and 24.2 IU/mg, respectively.

(3) Endotoxin Contamination Assay

The combined INDH1 and INDH2 enzyme was also analyzed for endotoxin contamination levels using the limulus amoebocyte lysate (LAL) assay as incorporated into PYROTEL (Associates of Cape Cod, INC., Woods Hole, Mass.) according to the manufacturer's instructions. The endotoxin level of purified INDH enzyme containing the combined INDH1 and INDH2 enzymes was about 0.04 nanograms (ng) of endotoxin per International Unit (IU) of Specific INDH Activity.

2. Immobilization of INDH to a Solid Support

Four hundred sixty-four grams of dry silica beads (R-648; Manville Corp., Denver, Colo.) were added to approximately 700 mls of pyrogen-free water contained in a 6 liter-capacity pyrogen-free process cartridge. The beads were repeatedly washed with 800 mls of pyrogen-free water until the wash solution remained clear, typically about 3-4 washes. The beads were then washed with 3.2 liters of acidic water titrated to pH 3.5 with hydrochloric acid. Thereafter, four liters of a heated (82-85 C.) 3-aminopropyltriethoxysilane solution, pH 3.5±0.1, were recirculated through the beads at a rate of 1 l/min for a total of three hours. The temperature of the solution was maintained at 82-85 C. throughout the entire recirculation procedure. The 3-aminopropyltriethoxysilane solution was prepared by adding, in a dropwise fashion, 88 mls of 3-aminopropyltriethoxysilane to 3.2 liters of pyrogen-free water. Simultaneously with the addition of the silane, 6N hydrochloric acid was added in droplets so as to maintain the pH of the solution between 3.0 and 7.0. The pH of the solution was then adjusted to 3.5 ±0.1 with either 1N hydrochloric acid or 1N sodium hydroxide.

Following the recirculation procedure, the 3-aminopropyltriethoxysilane solution was drained out of the process cartridge and the beads washed with at least 8 liters of pyrogen-free water, followed by at least 3.2 liters of 0.2M sodium acetate at pH 5.5. After draining off the excess sodium acetate buffer, the beads were washed with 2.08 liters of a 3% (v/v) glutaraldehyde solution adjusted to pH 5.5±0.1 with 1N sodium hydroxide and containing 5 mls of 2M sodium acetate, pH 5.5. The glutaraldehyde solution was recycled through the beads at a flow rate of 1 l/min for 1 hr at room temperature. During the entire recycling procedure, the pH was maintained at 5.5±0.1 with 1N sodium hydroxide. The glutaraldehyde solution was drained off the beads and the beads were then washed with a minimum of 21 liters of pyrogen-free water. Washing continued until the pH of the wash water was 7.0±0.5, and the aldehyde concentration of the wash water was less than 5 ppm. The water was drained off the beads and the beads contacted with resuspended in 2.4 liters of 0.2M sodium acetate buffer, pH 5.5, to form washed beads.

730 mg (18,675 IU) of combined INDH1 and INDH2 enzyme, prepared according to Example 1b, were admixed with approximately 100 mls of 4 C. 0.2M sodium acetate buffer, pH 5.5, to form an INDH immobilization buffer. Buffer in contact with the washed beads was drained from the process cartridge containing the washed beads. Thereafter, INDH immobilization buffer was recirculated through the washed beads at a flow rate of 1 l/min for 1-4 hours at 4 C. to coat the beads with INDH and form INDH-coated beads. Recirculation continued until the INDH enzyme activity of the INDH-immobilization buffer fell to less than 3% of its starting level, when measured in the NATA assay of Example 1c. The INDH-coated beads were washed with 5 liters of a lysine buffer containing 0.15M L-lysine monohydrochloride in 0.1M sodium phosphate, pH 7.5, for 1 hr at a recirculation rate of 1 l/min. Throughout the wash procedure, the pH of the lysine buffer was maintained at 7.5±0.1 using either 1N sodium hydroxide or 1N hydrochloric acid. The lysine buffer was drained off of beads and the beads sequentially washed in 2.4 liters of 2M sodium chloride in 0.1M sodium phosphate, pH 7.5, 2.4 liters of 0.1M sodium acetate, pH 4.5, and 2.4 liters of 0.9% (w/v) sodium chloride, pH 5.0 to form an immobilized INDH composition. The immobilized INDH composition can be used immediately or transferred to sterile, pyrogen-free glass bottles and stored for later use at 4 C. in 0.9% (w/v) sodium chloride, pH 5.0.

The resulting immobilized INDH composition, when tested using the above NATA assay, exhibited 5.7 IU per ml of packed silica beads (i.e., per ml of immobilized INDH composition). Because the silica beads form a matrix having a packed density of about 0.38 gms of beads per ml of packed matrix, an immobilized INDH composition so prepared has about 15 IU per gm of packed matrix.

3. Characterization of Tryptophan Depletion in Patient's Plasma Using an Immobilized INDH Composition a. Depletion of Tryptophan from Plasma Immobilized INDH composition prepared in Example 2 was transferred into a flow-through cartridge (type-size) such that the cartridge contained about 56 mls packed silica beads and about 320 IU INDH enzyme activity. The cartridge was then connected in series with a patient's circulatory system and with a continuous flow plasma pheresis device such that the patient's plasma could be diverted from the blood stream, through the cartridge and back into the patient's circulation, thereby effectively exposing a patient's plasma to the contents of the cartridge. Using this plasma diversion system, an adult patient's blood was treated daily for 21 consecutive days, each treatment lasting 4 hours with an average flow rate though the cartridge of 80 ml plasma per min. Plasma tryptophan levels were measured by the NATA assay of Example 1c by sampling the blood immediately before and after treatment on each day, and the results of the treatment are shown in Table 2.

TABLE 2

| | Blood Level of L-Tryptophan | | |
|---|---|---|---|
| Treatment Days | Pre-TRP[1] (µg/ml) | Decrease Pre-TRP | Percent Decrease Post-TRP[2] |
| 1 | 12.7 | | |
| 2 | 8.0 | 0.7 | 91.3 |
| 3 | 5.3 | 0 | 100 |
| 4 | 5.0 | 1.4 | 72.0 |
| 5 | 2.8 | 0 | 100 |

TABLE 2-continued

Blood Level of L-Tryptophan

| Treatment Days | Pre-TRP[1] (μg/ml) | Decrease Pre-TRP | Percent Decrease Post-TRP[2] |
|---|---|---|---|
| 6 | 6.0 | 0.7 | 88.3 |
| 7 | 1.1 | N.D.[3] | N.D. |
| 8 | 1.3 | N.D. | N.D. |
| 9 | 3.3 | 0 | 100 |
| 10 | 1.1 | 1.0 | 9.1 |
| 11 | 0.8 | 0 | 100 |
| 12 | 0.8 | 0.3 | 62.5 |
| 13 | 0 | 1.3 | 0 |
| 14 | 0 | N.D. | N.D. |
| 15 | 0 | N.D. | N.D. |
| 16 | 1.5 | 0 | 100 |
| 17 | 1.4 | 0 | 100 |
| 18 | 0.8 | 0 | 100 |
| 19 | 0.8 | 0.1 | 87.5 |
| 20 | 0.8 | 0.6 | 25.0 |

[1]Pre-TRP indicates pretreatment.
[2]Post-TRP indicates post-treatment.
[3]N.D. indicates no data.

The data in Table 2 show that recirculation of patient's blood through a cartridge containing immobilized INDH enzyme is an effective method of acutely reducing blood levels of L-tryptophan. The data further show that sequential daily treatment with an immobilized INDH enzyme of this invention is effective as a chronic method for maintaining blood L-tryptophan at reduced levels.

b. Toxicity of an Immobilized INDH Composition

In view of the potential severity of a patient's response upon exposure to endotoxin, a cartridge prepared as in Example 3a was evaluated for toxicity effects when a plasma treatment was conducted as in Example 3a. As a control, a similar cartridge was prepared using an inferior INDH enzyme preparation. The inferior INDH preparation was produced as in Example 1b except that the combined INDH1 and INDH2 pooled fraction was carried through ultrafiltration to form substantially isolated INDH enzyme, but was not further processed in the DOC detergent chromatography steps. The inferior INDH preparation so produced exhibited a specific activity of about 5 IU/mg and an endotoxin level of about 5.6 to 42.3 ng endotoxin per IU of INDH activity. The inferior INDH preparation was immobilized to silica beads as in Example 2 and then placed into a cartridge for plasma treatment.

Seven patients were treated by plasma recirculation for 4 hours as in Example 3a, using the above prepared cartridges. A toxicity level rating was assigned to each patient after the 4 hour treatment on the basis of symptoms of allergy, fever and sweating, and is shown in Table 3.

TABLE 3

Toxicity of Immobilized INDH Preparations

| Patient[a] | Endotoxin[b] (ng/cartridge) | Allergy | Fever | Sweating |
|---|---|---|---|---|
| 1 | 4770–35909 | 1–2 | 1–2 | 1–2 |
| 2 | 4770–35909 | 1–2 | 1–2 | 1–2 |
| 3 | 4770–35909 | 1 | 3 | 1 |
| 4 | 4770–35909 | 2 | 2 | 2 |
| 5 | 14–28 | 0 | 0 | 0 |
| 6 | 14–28 | 0 | 0 | 0 |
| 7 | 14–28 | 0 | 0 | 0 |

[a]Patients 1–4 were pre-medicated prior to cartridge treatment with 50 mg Benadryl and 60 mg Tylenol per day to minimize possible toxicity, whereas patients 5–7 were not pre-medicated.
[b]Endotoxin content per cartridge is expressed as a range due to the manner by which endotoxin is measured using the LAL assay described in Example 1c.
[c]The toxicity level was determined using the toxicity rating scale shown in Table 4.

The data in Table 3 demonstrates that patients 5–7 treated with a cartridge containing immobilized INDH composition demonstrated no clinical signs of toxicity during treatment, whereas patients 1–4 treated with the control cartridge having unacceptable levels of endotoxin produced unacceptable levels of endotoxin toxicity.

These results are consistent with the low levels of endotoxin shown to be associated with purified INDH enzyme used to prepare an immobilized INDH composition.

TABLE 4

| Type | 0 | 1 | 2 | 3 | 4 |
|---|---|---|---|---|---|
| Allergy | none change | transient rash drug fever <38° C. <100.4° F., mild mild shaking | urticaria, drug fever >38°C., 100.4° F., mild bronchospasm mod. shaking | serum sickness bronchospasm, parenteral meds severe shaking req. medication | anaphylaxis |
| Fever | none | <38° C., <100.4° F. | 38–40° C. 100.4–104° F. | >40° C., >104° F. | fever + hypotension |
| Sweating | none or normal | occasional | persistent, but intervention req'd | requires intervention | requires discontinuation of Rx | c. Stability of an Immobilized INDH Composition

A cartridge was prepared and used to treat a patient's plasma as described in Example 3a, except that a single 4 hour treatment was conducted, and the tryptophan levels were measured in the plasma immediately proximal (pre) and immediately distal (post) to the cartridge device at 1 hour intervals throughout the 4 hours of treatment. The detected tryptophan levels in two patients treated in this manner is shown in Table 5.

TABLE 5

Stability of Immobilized INDH

| Time (minutes) | Pre-Device ug/ml | Post Device ug/ml | Percent Change |
|---|---|---|---|
| Patient A | | | |
| 60 | 6.84 | 0 | 100 |
| 120 | 4.78 | 0 | 100 |
| 180 | 4.49 | 0 | 100 |
| 240 | 4.97 | 0 | 100 |
| Patient B | | | |
| 60 | 2.0 | 0 | 100 |
| 120 | 0.3 | 0 | 100 |
| 180 | 1.1 | 0 | 100 |
| 240 | 0.9 | 0 | 100 |

The data shows that immobilized INDH enzyme is stable over the entire 4 hour treatment period during which the enzyme is exposed to the plasma fluid. The depletion of tryptophan was as complete after 4 hours of treatment as during the first hour of treatment. Taken together with the findings of Examples 3a and 3b, these data show that the INDH enzymes of this invention provide a non-toxic, effective, efficient and stable method for reducing L-tryptophan levels of body fluids.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. An indolyl-3-alkane alpha-hydroxylase (INDH) composition obtainable from Pseudomonas XA, which INDH composition:
   a) comprises a substantially isolated INDH selected from the group consisting of:
      i) an INDH1 having first, second and third protein subunits, said first protein subunit having a molecular weight of about 75,000 daltons, said second protein subunit having a molecular weight of about 34,500 daltons, and said third protein subunit having a molecular weight of about 32,500 daltons, all as determined by sodium dodecyl sulfate-polyacrylamide gel electrophoresis; and
      ii) an INDH2 having first, second and third protein subunits, said first protein subunit having a molecular weight of about 60,000 daltons, said second protein subunit having a molecular weight of about 44,000 daltons, and said third protein subunit having a molecular weight of about 42,000 daltons as determined by sodium dodecyl sulfate-polyacrylamide gel electrophoresis;
   b) has a Specific INDH Activity of at least 10 International Units of INDH activity per milligram of protein in the composition; and
   c) contains less than 1 nanogram of endotoxin per International Unit of Specific INDH Activity.

2. The INDH composition of claim 1 wherein said composition comprises a combination of INDH1 and INDH2 in a mass ratio of about 50 percent each.

3. The INDH composition of claim 1 wherein said composition has a Specific INDH Activity of about 25 International Units of INDH activity per milligram of protein in said composition.

4. The INDH composition of claim 1 wherein said INDH contains less than 0.04 nanograms of endotoxin per International Unit of Specific INDH Activity.

5. An immobilized indolyl-3-alkane alpha-hydroxylase (INDH) composition, comprising:
   a) an insoluble matrix; and
   b) an INDH composition obtainable from Pseudomonas XA and affixed to the insoluble matrix, wherein said INDH composition:
      i) comprises a substantially isolated INDH selected from the group consisting of:
         1) an INDH1 having first, second and third protein subunits, said first protein subunit having a molecular weight of about 75,000 daltons, said second protein subunit having a molecular weight of about 34,500 daltons, and said third protein subunit having a molecular weight of about 32,500 daltons, all as determined by sodium dodecyl sulfate-polyacrylamide gel electrophoresis; and
         2) an INDH2 having first, second and third protein subunits, said first protein subunit having a molecular weight of about 60,000 daltons, said second protein subunit having a molecular weight of about 44,000 daltons, and said third protein subunit having a molecular weight of about 42,000 daltons as determined by sodium dodecyl sulfate-polyacrylamide gel electrophoresis;
      ii) has a Specific INDH Activity of at least 10 International Units of INDH activity per milligram of protein in the composition; and
      iii) contains less than 1 nanogram of endotoxin per International Unit of Specific INDH Activity, said immobilized INDH composition having at least 2.5 International Units of INDH activity per gram of immobilized INDH composition and having less than 10 nanograms of endotoxin per International Unit of INDH activity present in the immobilized INDH composition.

6. The immobilized INDH composition of claim 5 wherein said immobilized INDH composition has about 15 International Units of INDH activity per gram of said immobilized INDH composition.

7. The immobilized INDH composition of claim 5 wherein said immobilized INDH composition contains less than 0.1 nanograms of endotoxin per International Unit of INDH activity present in said immobilized INDH composition.

8. The immobilized INDH composition of claim 5 wherein said insoluble matrix is comprised of silica beads.

* * * * *